United States Patent

Furukawa et al.

[11] Patent Number: 5,834,612
[45] Date of Patent: Nov. 10, 1998

[54] FLUORINE-CONTAINING ORGANIC COMPOUND

[75] Inventors: Yutaka Furukawa, Yokohama; Seisaku Kumai, Fujisawa, both of Japan; Jeffery A. Cooke, Peeksville, N.Y.; Gerald J. Murphy, Hopewell Junction, N.Y.; George A. Policello, Ossining, N.Y.

[73] Assignees: Asahi Glass Company Ltd., Tokyo, Japan; OSI Specialties, Inc., Greenwich, Conn.

[21] Appl. No.: 855,947

[22] Filed: May 14, 1997

[30] Foreign Application Priority Data

May 18, 1996 [JP] Japan .................................. 8-148426

[51] Int. Cl.$^6$ ........................................................ C07F 7/08
[52] U.S. Cl. ............................ 556/448; 528/15; 568/685
[58] Field of Search ........................... 568/685; 556/448; 528/15

[56] References Cited

U.S. PATENT DOCUMENTS

| | | | |
|---|---|---|---|
| 2,749,369 | 6/1956 | Lyon et al. | 568/685 |
| 2,781,405 | 2/1957 | Shukys | 568/685 |
| 3,077,501 | 2/1963 | Oakes | 568/685 |
| 4,968,828 | 11/1990 | Yamamoto | 556/448 |
| 5,043,464 | 8/1991 | Yamamoto | 556/448 X |
| 5,344,580 | 9/1994 | Von Werner | 568/685 X |
| 5,412,135 | 5/1995 | Fukuda et al. | 556/448 |
| 5,568,239 | 10/1996 | Furukawa et al. | |
| 5,663,399 | 9/1997 | Furukawa et al. | |
| 5,700,898 | 12/1997 | Okada et al. | 556/448 X |

FOREIGN PATENT DOCUMENTS 7-53719  2/1995  Japan .

*Primary Examiner*—Paul F. Shaver
*Attorney, Agent, or Firm*—Oblon, Spivak, McClelland, Maier & Neustadt, P.C.

[57] ABSTRACT

A fluorine-containing organic compound of the following formula (1):

$$R^f CH_2CH_2CH_2OCH_2CH=CH_2 \qquad (1)$$

wherein $R^f$ is a $C_{1-20}$ fluoroalkyl group.

11 Claims, No Drawings

FLUORINE-CONTAINING ORGANIC COMPOUND

BACKGROUND OF THE INVENTION

1. Field of the Invention

The present invention relates to a novel fluorine-containing organic compound. The fluorine-containing organic compound of the present invention is a useful compound which can be used as a starting material or intermediate for various functional materials such as water and oil repellants, surface active agents, pharmaceuticals and agricultural chemicals.

2. Discussion of Background

A compound having a carbon-carbon double bond at a terminal of a fluoroalkyl group, is widely used as a polymerizable monomer or an intermediate for pharmaceuticals or agricultural chemicals, since it is expected to provide various functions attributable to the fluoroalkyl group. For example, a fluorine-containing silicone compound obtained by reacting such a compound with a hydrosilicone compound, is industrially widely used for various industrial base materials which are required to have water and oil repellency, stain-proofing properties, release properties or the like, or as a starting material thereof.

JP-B-6-78345 discloses $C_kF_{2k+1}$—CH=$CH_2$ (wherein k is an integer of from 4 to 10), or $R^fCH_2OCH_2$—CH=$CH_2$ (wherein $R^f$ is a $C_{4-10}$ perfluoroalkyl group or a $C_{5-14}$ perfluoropolyether group), as a fluorine-containing organic compound useful for producing a fluorine-containing organic silicone compound.

JP-A-7-216090 discloses a fluorine-modified silicone, a process for its production and a cosmetic containing it, and the same publication discloses a compound such as $C_3F_7C(CF_3)_2CH_2CH$=$CH_2$, as a fluorine-containing compound useful for hydrosilylation.

JP-A-7-53719 discloses a process for producing a fluorine-containing organopolysiloxane compound by reacting a certain specific organopolysiloxane with a fluorine-containing olefin, and as such a fluorine-containing olefin, $C_8F_{17}CH_2CH$=$CH_2$ or n—$C_3F_7OCH_2CH$=$CH_2$ is specifically disclosed.

JP-A-4-99780 specifically discloses $R^f$—$CH_2OCH_2$—CH=$CH_2$ wherein $R^f$ is a $C_{4-10}$ perfluoroalkyl group, as a fluorine-containing organic compound to be used for producing an organic silicone compound.

However, when $C_6F_{13}CH$=$CH_2$ (k is 6 in the above identified formula) is used as the fluorine-containing organic compound in JP-B-6-78345, there is a problem that such a compound is poor in the reactivity. Further, when $C_3F_7OCF(CF_3)CH_2OCH_2CH$=$CH_2$ ($R^f$ is $C_3F_7OCF(CF_3)$ in the above identified formula) will be used, there will be a problem that such a compound is expensive and hardly available, a multi-step process is required for its preparation, and by-products are substantial during the preparation.

$C_3F_7C(CF_3)_2CH_2CH$=$CH_2$ disclosed in JP-A-7-216090 is prepared by oligomerization of hexafluoropropene, but has problems that by-products are substantial, and control of the reaction is difficult.

$C_8F_{17}CH_2CH$=$CH_2$ and n—$C_3F_7OCH_2CH$=$CH_2$ disclosed in JP-A-7-53719 have problems such that the synthesis is difficult, and it is practically difficult to produce them in a large amount on an industrial scale.

Further, when $R^fCH_2OCH_2$—CH=$CH_2$ (wherein $R^f$ is a $C_{4-10}$ perfluoroalkyl group) as disclosed in JP-A-4-99780 is used, there will be a drawback that no adequate water repellency can be obtained.

SUMMARY OF THE INVENTION

As a result of an extensive study to solve the above problems, the present inventors have found it possible to produce a fluorine-containing compound of the following formula (1) at a low cost and to carry out hydrosilylation efficiently. The present invention has been accomplished on the basis of these discoveries.

Namely, the present invention provides a fluorine-containing organic compound of the following formula (1):

wherein $R^f$ is a $C_{1-20}$ fluoroalkyl group.

DETAILED DESCRIPTION OF THE PREFERRED EMBODIMENTS

In the fluorine-containing organic compound of the above formula (1) (hereinafter sometimes referred to as "compound (1)"), the number of carbon atoms in $R^f$ is preferably from 3 to 16, more preferably from 4 to 12.

The fluoroalkyl group is a group having at least one hydrogen atom of an alkyl group substituted by a fluorine atom and preferably a group having at least two hydrogen atoms of an alkyl group substituted by fluorine atoms. In the present invention, the fluoroalkyl group may be such that at least one carbon atom of an alkyl group is substituted by an ether type oxygen atom or a thioether type sulfur atom, or —NH— may be inserted between carbon atoms of a carbon-carbon bond.

The fluoroalkyl group is preferably a polyfluoroalkyl group having at least two hydrogen atoms of an alkyl group substituted by fluorine atoms. The number of fluorine atoms in the polyfluoroalkyl group is preferably at least 60%, more preferably at least 80%, most preferably substantially 100%, as represented by (the number of fluorine atoms in the polyfluoroalkyl group)/(the number of hydrogen atoms in an alkyl group having the same number of carbon atoms as the polyfluoroalkyl group)×100(%).

The fluoroalkyl group may have either a straight-chain structure or a branched chain structure, but preferably has a straight-chain structure. When it has a branched structure, the branched portion is preferably a short chain of from 1 to 3 carbon atoms.

Compound (1) of the present invention is preferably a compound wherein at least one fluorine atom is directly bonded to the carbon atom directly bonded to —$CH_2CH_2CH_2OCH_2CH$=$CH_2$, among carbon atoms constituting $R^f$.

The fluoroalkyl group is preferably a group having substantially all of hydrogen atoms of an alkyl group substituted by fluorine atoms (hereinafter referred to as "a perfluoroalkyl group"). Particularly preferred is a straight-chain perfluoroalkyl group wherein $R^f$ is represented by $CF_3(CF_2)_n$— wherein n is an integer of from 0 to 19, preferably from 5 to 11, which represents the number of carbon atoms.

Specific examples of $R^f$ will be given below. The following specific examples include the respective structure-isomeric groups.

$C_4F_9$— (including structure-isomeric groups such as $CF_3(CF_2)_3$—, $(CF_3)_2CFCF_2$—, $(CF_3)_3C$— and $CF_3CF_2CF(CF_3)$—), $C_5F_{11}$—(including structure-isomeric groups such as $CF_3(CF_2)_4$—, $(CF_3)_2CF(CF_2)_2$—, $(CF_3)_3CCF_2$— and $CF_3(CF_2)_2CFCF_3$—), $C_6F_{13}$— (including structure-isomeric groups such as $CF_3(CF_2)_2C$ $(CF_3)_2$—), $C_8F_{17}$—, $C_{10}F_{21}$—, $C_{12}F_{25}$—, $C_{14}F_{29}$—, $C_{16}F_{33}$—, $C_{18}F_{37}$—, $C_{20}F_{41}$—, $(CF_3)_2CFC_sF_{2s}$— (wherein s is an integer of from 1 to 17), $HC_tF_{2t}$— (wherein t is an integer of from 1 to 20), $CF_3(CF_2)_4OCF(CF_3)$—, $F[CF(CF_3)CF_2O]_uCF(CF_3)CF_2CF_2$— (wherein u is an integer of from 1 to 5), $F[CF(CF_3)CF_2O]_rCF(CF_3)$— (wherein r is an integer of from 1 to 6), $F(CF_2CF_2CF_2O)_vCF_2CF_2$— (wherein v is an integer of from 1 to 6), and $F(CF_2CF_2O)_wCF_2CF_2$— (wherein w is an integer of from 1 to 9).

A fluorine-containing organic compound of the above formula (1) wherein $R^f$ is a straight-chain perfluoroalkyl group, as a preferred example of the compound of the present invention, is represented by the following formula (2):

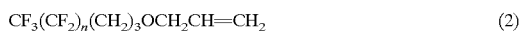

$$CF_3(CF_2)_n(CH_2)_3OCH_2CH=CH_2 \qquad (2)$$

wherein n is an integer of from 0 to 19, preferably from 5 to 11, which represents the number of carbon atoms.

The following compounds may be mentioned as specific examples of the fluorine-containing organic compound of the above formula (1) of the present invention.

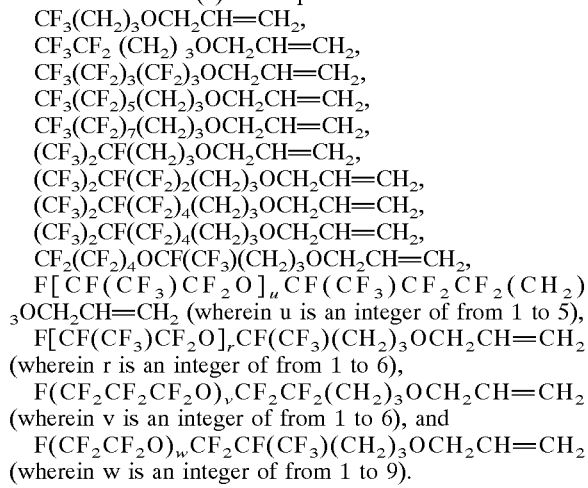

$CF_3(CH_2)_3OCH_2CH=CH_2$,
$CF_3CF_2(CH_2)_3OCH_2CH=CH_2$,
$CF_3(CF_2)_3(CH_2)_3OCH_2CH=CH_2$,
$CF_3(CF_2)_5(CH_2)_3OCH_2CH=CH_2$,
$CF_3(CF_2)_7(CH_2)_3OCH_2CH=CH_2$,
$(CF_3)_2CF(CH_2)_3OCH_2CH=CH_2$,
$(CF_3)_2CF(CF_2)_2(CH_2)_3OCH_2CH=CH_2$,
$(CF_3)_2CF(CF_2)_4(CH_2)_3OCH_2CH=CH_2$,
$(CF_3)_2CF(CF_2)_4(CH_2)_3OCH_2CH=CH_2$,
$CF_2(CF_2)_4OCF(CF_3)(CH_2)_3OCH_2CH=CH_2$,
$F[CF(CF_3)CF_2O]_uCF(CF_3)CF_2CF_2(CH_2)_3OCH_2CH=CH_2$ (wherein u is an integer of from 1 to 5),
$F[CF(CF_3)CF_2O]_rCF(CF_3)(CH_2)_3OCH_2CH=CH_2$ (wherein r is an integer of from 1 to 6),
$F(CF_2CF_2CF_2O)_vCF_2CF_2(CH_2)_3OCH_2CH=CH_2$ (wherein v is an integer of from 1 to 6), and
$F(CF_2CF_2O)_wCF_2CF(CF_3)(CH_2)_3OCH_2CH=CH_2$ (wherein w is an integer of from 1 to 9).

A method for producing compound (1) of the present invention is not particularly limited. For example, a method may be mentioned wherein a 3-fluoroalkylpropanol and an allyl halide are reacted in the presence of a phase transfer catalyst and an alkali. The allyl halide is preferably allyl chloride or allyl bromide, particularly preferably allyl chloride. The phase transfer catalyst is preferably a quarternary ammonium salt or phosphonium salt having a hydrocarbon group, particularly preferably tetra-n-butylammonium bromide, tetra-n-butylammonium sulfite, tetraphenylphosphonium bromide or tetra-n-butylphosphonium bromide, more preferably tetra-n-butylammonium bromide or tetra-n-butylammonium sulfite. The alkali is preferably an alkali metal hydroxide, such as sodium hydroxide or potassium hydroxide. The alkali metal hydroxide is preferably used in the form of an aqueous solution, and the concentration of such an aqueous solution is preferably from 20 to 50 wt %. The amount of the phase transfer catalyst is preferably from 0.1 to 10 mol % to compound (1). The above reaction may be carried out in the presence of a solvent. As such a solvent, methylene chloride is preferred.

Compound (1) of the present invention is a compound useful as an intermediate or a starting material for various functional materials such as water and oil repellants, surface active agents, pharmaceuticals and agricultural chemicals. It is possible to obtain a fluorine-containing silicone compound excellent in water and oil repellency, stain-proofing properties, etc., for example, by subjecting compound (1) of the present invention and a hydrosilicone compound having a hydrogen atom directly bonded to a silicon atom (Si—H) to a hydrosilylation reaction. Compound (1) of the present invention is highly reactive, and the hydrosilylation reaction readily proceeds, whereby a fluorosilicone compound having a fluoroalkyl group introduced can be obtained.

Here, "the hydrosilicone compound having a hydrogen atom directly bonded to a silicon atom (Si—H)" may be a known or well known compound which has one or more Si—H moieties as partial structures in the molecule of a silicone compound. Such a fluorosilicone compound is preferably a silicone compound comprising, as structural units of the silicone compound, hydrosiloxane units such as $R^aHSiO_{2/2}$ units, $(R^b)_2HSiO_{1/2}$ units or $HSiO_{3/2}$ units, wherein each of $R^a$ and $R^b$ is a monovalent hydrocarbon group, preferably a $C_{1-3}$ alkyl group, $C_6H_5$— or $C_6H_5CH_2CH_2$—, particularly preferably a methyl group.

When the hydrosilicone compound contains organosiloxane units other than hydrosiloxane units, such units are preferably $(R^c)_3SiO_{1/2}$ units, $(R^d)_2SiO_{2/2}$ units or $R^eSiO_{3/2}$ units. Here, each of $R^c$ to $R^e$ is a monovalent hydrocarbon group, preferably a $C_{1-3}$ alkyl group, $C_6H_5$— or $C_6H_5CH_2CH_2$—, particularly preferably a methyl group.

The hydrosilicone compound may have either a cyclic or linear (straight-chain or branched chain) structure, preferably a cyclic or linear (straight-chain or branched chain) structure, more preferably a straight-chain structure.

In the present invention, the hydrosilicone compound is preferably a hydrosilicone compound represented by the average compositional formula (3):

$$(R^7)_c(H)_dSiO_{(4-c-d)/2} \qquad (3)$$

In the above formula (3), $0 \leq c < 4$, $0 < d < 4$, and $0 < c+d \leq 4$, and $R^7$ is a monovalent organic group, preferably a monovalent hydrocarbon group, more preferably a $C_{1-3}$ alkyl group, $C_6H_5$— or $C_6H_5CH_2CH_2$—, most preferably a methyl group.

The hydrosilicone compound of the average compositional formula (3) may, for example, be a hydrosilicone compound of the following formula (4), or a hydrosilicone compound such as $(CH_3)_2HSiO(CH_2)_pSiO(CH_3)_2H$ (wherein p is an integer of at least 1), preferably the compound of the formula (4).

$$(R^7)_3SiO.[Si(R^7)_2O]_q.[SiH(R^7)O]_r.Si(R^7)_3 \qquad (4)$$

In the formula (4), $R^7$ is as defined above, q is an integer of 0 or more, and r is an integer of 1 or more. In the above formula, $R^7$ is particularly preferably a methyl group. The silicone compound of the formula (4) may be either a block polymer or a random polymer.

Compound (1) of the present invention is subjected to hydrosilylation with a hydrosilicone compound having one or more hydrogen atoms directly bonded to a silicon atom to obtain a fluorine-containing hydrosilicone compound excellent in water repellency, stain-proofing properties, etc.

Compound (1) to be used for the hydrosilylation may be a mixture of two or more compounds having fluoroalkyl groups of different structures. When two or more compounds are used, they are preferably those having fluoroalkyl groups having different numbers of carbon atoms.

The reaction (hereinafter referred to as "the hydrosilylation") of compound (1) of the present invention with a hydrosilicone compound may be carried out, for example, as follows.

Namely, compound (1) is reacted with a hydrosilicone compound having at least one hydrogen atom bonded to a silicon atom to obtain a reaction product containing a hydrosilicone compound having a $R^fCH_2CH_2CH_2OCH_2CH_2CH_2$— group bonded to a silicon atom and a hydrogen atom bonded to a silicon atom. Further, in a case where the reaction product contains a certain amount of unreacted hydrogen atoms bonded to silicon atoms, such a product may further be reacted with $CH_2$=$CHR^8$ (wherein $R^8$ is a hydrogen atom or a $C_{1-6}$ organic group) or the like to obtain a fluorine-containing silicone compound which contains substantially no hydrogen atom bonded to a silicon atom.

In the above described hydrosilylation, addition of a hydrogen atom directly bonded to a silicon atom to the above formula (1) to form a silicone compound having a $R^fCH_2CH_2CH_2OCH_2CH_2CH_2$— group directly bonded to a silicon atom.

In the hydrosilylation of compound (1) with the hydrosilicone compound, it is important that compound (1) is a compound having a linking group (in the case of the present invention, —$CH_2CH_2CH_2O$—$CH_2$—) between the $R^f$ group and the unsaturated —$CH$=$CH_2$ group. A compound having no such linking group, for example, a group of the formula $C_8F_{17}CH$=$CH_2$, has a drawback that the addition reaction with the hydrosilicone compound tends to hardly proceed.

In the reaction of compound (1) with the above hydrosilicone compound, it is preferred to use a catalyst. As such a catalyst, a catalyst containing a transition metal is preferred, and a catalyst containing platinum, rhodium or cobalt is particularly preferred. The reaction temperature is usually preferably within a range of from 0° to 100° C., and the reaction time is preferably from 0.5 to 10 hours. The amount of the catalyst is usually preferably from 1 to 100 ppm in the reaction system.

In the following description, silicone compounds having a $R^f(CH_2)_3OCH_2CH_2CH_2$— group bonded to a silicon atom, formed by the reaction of compound (1) with a hydrosilicone compound will be referred to generally as "fluorine-containing silicone compounds". Preferred as a fluorine-containing silicone compound is a fluorine-containing silicone compound of the following formula (5) which is obtainable by reacting compound (1) with a hydrosilicone compound of the above formula (4).

$(R^7)_3SiO.[Si(R^7)_2O]_q.[SiH(R^7)O]_{r-s}.$
$[Si(CH_2CH_2CH_2OCH_2CH_2CH_2R^f)(R^7)O]_s.(R^7)_3$ (5)

In the formula (5), q is an integer of at least 0, r is an integer of at least 1, and s is an integer of at least 1, provided that r≧s.

The ratio of the two compounds in the reaction of compound (1) with the hydrosilicone compound, may be optionally varied depending upon the desired fluorine-containing silicone compound and is not particularly limited.

When all hydrogen atoms bonded to silicon atoms are to be hydrosilylated, it is usually preferred to use compound (1) in an amount of at least 1 equivalent to the amount of hydrogen atoms bonded to silicon atoms in the hydrosilicone compound. However, if the amount is too much, it will be cumbersome to remove the excess amount from the reaction product. Therefore, it is particularly preferably from 1.1 to 2 equivalents.

When the fluorine-containing silicone compound has a hydrogen atom directly bonded to a silicon atom, gelation is likely to take place under heating. Accordingly, in such a case, the product is preferably further subjected to hydrosilylation with a compound having a carbon-carbon double bond other than compound (1). As such a compound having a carbon-carbon double bond other than compound (1), the compound of the formula $CH_2$=$CHR^8$ (wherein $R^8$ is a hydrogen atom or a $C_{1-6}$ organic group) or an unsaturated compound having alkylene oxide units, of the formula (6), may be used.

$CH_2$=$CH(OCH_2CH_2)_a[OCH_2CH(CH_3)]_bOR^9$ (6)

wherein a is an integer of at least 0, b is an integer of at least 0, provided that either a or b is an integer of at least 1, and $R^9$ is a hydrogen atom or a $C_{1-3}$ alkyl group.

The reaction product with the unsaturated compound having alkylene oxide units can be used as a surface active agent or as a water and oil repellant.

The reaction time may optionally be varied depending upon the types of the starting materials, etc., but is usually preferably from 3 to 5 hours. The reaction pressure is preferably atmospheric pressure or elevated pressure.

The method of hydrosilylation is far efficient as compared with a conventional method of ring-opening polymerization of a fluoroalkyl group-containing siloxane trimer and has a merit that the production cost can be made low.

The fluorine-containing silicone compound thus obtained is useful for stain-proofing oil for copying rolls, various lubricating oils including refrigerator oil, vacuum pump oil or the like, various working oils including transmission oil, brake oil, coupling oil or the like, vibration-deadening oils for automobile or airplane instruments, pickup for player or the like, damping oils for dash pot, shock absorber or the like, lubricating agents, repellents and release agents for heat transfer recorded image-receiving material, magnetic recording medium, magnetic head, impregnated bearing or the like, roll compositions or their surface-coating agents for copying machines, printers or the like, blending agents for shampoo, rinse, or other various make up cosmetic materials, treating agents for various powders, water repellent-oil repellent agents, deep color-processing agents, lubrication-imparting agents for fabrics, insulating oils including transformer oils, condenser oils, cable oils or the like, various additives including leveling agents, anti-blocking agents, irregular color-preventing agents, orange peel-preventing agents or the like for polymer materials including plastics, paints or the like, plasticizers or modifiers for rubber or resins, anti-foaming agents, base oils for grease or compounds, foam stabilizers, blending oils for wax, toner treating agents, oil sealing agents, rust proofing agents, antistatic agents, anti-fogging agents, additives for pharmaceuticals, polishing materials, and the like. Thus, it is useful in various fields including fields of cosmetics, defoaming agents, surfactants and water and oil repellants.

Compound (1) of the present invention is not limited to the above mentioned applications and is expected to find a wider range of applications for other fluorine-containing materials or as a starting material thereof.

Now, the present invention will be described in further detail with reference to Examples. However, it should be understood that the present invention is by no means restricted to such specific Examples.

(Comparative Example 1) or $CF_3(CF_2)_2OCF(CF_3)CH_2OCH_2CH=CH_2$ (Comparative Example 2) was used. A compound of the following formula (9) was obtained in Comparative Example 1, and a compound of the following formula (10) was obtained in Comparative Example 2.

$$(CH_3)_3SiO.[Si(CH_3)_2O]_n.\{Si[(CH_2)_3(CF_2)_7CF_3](CH_3)O\}_{m/2}.\{Si[(CH_2)_5(OCH_2CH_2)_ROCH_3](CH_3)O\}_{m/2}.Si(CH_3)_3 \quad (9)$$

$$(CH_3)_3SiO.[Si(CH_3)_2O]_n.\{Si[(CH_2)_3OCH_2CF(CF_3)O(CF_2)_2.CF_3](CH_3)O\}_{m/2}.\{Si[(CH_2)_3(OCH_2CH_2)_ROCH_3](CH_3)O\}_{m/2}.Si(CH_3)_3 \quad (10)$$

EXAMPLE 1

Into a 5 l three-necked flask equipped with a thermometer, a reflux condenser and a dropping funnel, 1637 g (3.43 mol) of $CF_3(CF_2)_7(CH_2)_3OH$, 315 g (4.12 mol) of 3-chloropropene, 55.2 g (0.17 mol) of tetra-n-butylammonium bromide and 1080 g of methylene chloride were charged and stirred at 40° C. Then, 1370 g of a 50% sodium hydroxide aqueous solution was gradually added thereto by the dropping funnel. Then, the mixture was reacted at 40° C. for 24 hours and then subjected to separation into two phases. The organic layer was washed once with a dilute hydrochloric acid aqueous solution and then twice with water, followed by distillation to obtain $CF_3(CF_2)_7(CH_2)_3OCH_2CH=CH_2$ in an amount of 1505 g (yield: 84.8%, boiling point: 230° C.).

$^1$H-NMR (90 MHz, CDCl$_3$) δ (ppm): 1.7–2.0(2H,m,—CH$_2$), 2.0–2.4(2H,m,—CH$_2$—(CF$_2$)—), 3.3–3.5(2H,CH$_2$O, t,J=5.68 Hz), 3.9–4.0(2H,d,OCH$_2$,J=5.54 Hz,1.29 Hz), 5.0–5.4(2H,m,=CH$_2$), 5.7–6.1(1H,m,—CH=).

$^{19}$F-NMR (90 MHz, CDCl$_3$) δ (ppm): −81.7(CF$_3$), −115.((CF$_2$)CF$_3$), −122.5–124.1(CF$_2$, −126.9(CF$_2$CH$_2$)

EXAMPLE 2

Into a 1 l four-necked flask equipped with a stirrer, a Dimroth condenser, a thermometer and a dropping funnel, 500 g of methylhydrodienesiloxane compound of the following formula (7) was charged and stirred at 90° C.

$$(CH_3)_3SiO-[Si(CH_3)_2O]_n.[SiH(CH_3)O]_m.Si(CH_3)_3 \quad (7)$$

In the formula (7), n+m=30, and n/m=⅛.

Then, 240 g (0.45 mol) of $CF_3(CF_2)_7(CH_2)_3OCH_2CH=CH_2$ prepared in Example 1 and 1.0 g of an isopropanol solution containing 1% of chloroplatinic acid were gradually added thereto by the dropping funnel.

Then, 250 ml of toluene was added thereto. Thereafter, 142 g (0.4 mol) of $CH_3O(CH_2CH_2O)RCH_2CH=CH_2$ (wherein the average value of R is 6.6) and 3.4 g of an isopropanol solution containing 1% of chloroplatinic acid were gradually added thereto from the dropping funnel. Completion of the reaction was confirmed by disappearance of the H—Si stretching vibration (2150 cm$^{-1}$) by the infrared spectrophotometry.

The structure of the product was confirmed to be as shown by the following formula (8) by $^1$H-NMR.

$$(CH_3)_3SiO.[Si(CH_3)_2O]_n.\{Si[(CH_2)_3O(CH_2)_3(CF_2)_7CF_3(CH_3).O\}_{m/2}.\{Si[(CH_2)_3(OCH_2CH_2)_ROCH_3](CH_3)O\}_{m/2}.Si(CH_3)_3 \quad (8)$$

In the formula (8), the symbols are as defined above.

COMPARATIVE EXAMPLES 1 AND 2

The reaction was carried out in the same manner as in Example 2 except that instead of $CF_3(CF_2)_7(CH_2)_3OCH_2CH=CH_2$ in Example 2, $CF_3(CF_2)_7CH_2CH=CH_2$ In the formulas (9) and (10), the symbols are as defined above.

Evaluation

Compounds (8), (9) and (10) thus obtained were used for treatment of cloth. As the cloth to be treated, polyester yarn woven fabric was used. A treating bath was prepared by diluting compounds (8), (9) or (10) with methyl ethyl ketone so that the solid content concentration would be 1 wt %. The cloth to be treated i.e. the polyester yarn woven fabric was immersed in the bath and treated so that the solid content concentration to the weight of the cloth to be treated would be 1 wt %. Further, the treated cloth was uniformly squeezed at a squeezing rate of 60% and dried at 100° C. for 30 minutes. With respect to the treated cloth, the oil repellency and the hand and drape were evaluated. The results are shown in Table 4.

Evaluation of Water Repellency

Water repellency was measured by a water/isopropyl alcohol (IPA) test. One drop of each of test liquids of the grades as identified in the following Table 1, was put on the surface of the treated cloth, and the grade which did not penetrate was examined upon expiration of 30 seconds. When the evaluation was inbetween two grades, it was represented as belonging to the grade having a larger numerical value. Evaluation was made based on an average value of the results of the test represented ten times.

TABLE 1

| Grades | Water/IPA (weight ratio) |
|--------|--------------------------|
| 10 | 0/100 |
| 9 | 10/90 |
| 8 | 20/80 |
| 7 | 30/70 |
| 6 | 40/60 |
| 5 | 50/50 |
| 4 | 60/40 |
| 3 | 70/30 |
| 2 | 80/20 |
| 1 | 90/10 |
| 0 | 100/0 |

Oil Repellency Test

A few drops (diameter: about 4 mm) of each of the test solutions as identified in the following Table 2 were put on a test cloth, and the oil repellency was evaluated by the penetration state upon expiration of 30 seconds (AATCC-TM-118-966).

TABLE 2

| Oil repellency number | Test solution | Surface tension (dyn/cm/25° C.) |
|---|---|---|
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | Mixed solution of nujol and hexadecane (65/35 weight ratio) | — |
| 1 | Nujol | 31.2 |
| 0 | Less than 1 | — |

Evaluation of Hand and Drape

The difference from non-treated cloth was evaluated by a sensory test by five assessors. The evaluation standards were as follows.

TABLE 3

| Evaluation results | Evaluation standards |
|---|---|
| Very flexible | Remarkably flexible as compared with non-treated cloth |
| Flexible | Distinctly flexible as compared with non-treated cloth |
| Slightly flexible | Slightly flexible as compared with non-treated cloth |
| No change | Same as non-treated cloth |
| Slightly hard | Slightly harder than non-treated cloth |
| Hard | Distinctly harder than non-treated cloth |
| Very hard | Remarkably harder than non-treated cloth |

TABLE 4

| | Compound | Water repellency | Oil repellency | Hand and drape |
|---|---|---|---|---|
| Example 2 | (8) | 5 | 4 | Very flexible |
| Comparative Example 1 | (9) | 5 | 5 | Slightly hard |
| Comparative Example 2 | (10) | 2 | 1 | Slightly flexible |

The fluorine-containing organic compound of the present invention is a compound useful as a starting material or an intermediate for various functional materials such as water and oil repellants, surface active agents, pharmaceuticals or agricultural chemicals. Hydrosilylation of the fluorine-containing organic compound of the present invention with a silicone compound can be carried out efficiently and at a low cost.

What is claimed is:

1. A fluorine-containing organic compound of the following formula (1):

$$R^f CH_2CH_2CH_2OCH_2CH=CH_2 \quad (1)$$

wherein $R^f$ is a $C_{1-20}$ fluoroalkyl group.

2. The fluorine-containing organic compound according to claim 1, wherein in the formula (1), at least one fluorine atom is directly bonded to the carbon atom directly bonded to $—CH_2CH_2CH_2OCH_2CH=CH_2$, among carbon atoms constituting $R^f$.

3. The fluorine-containing organic compound according to claim 1, wherein in the formula (1), $R^f$ is a $C_{1-20}$ perfluoroalkyl group.

4. The fluorine-containing organic compound according to claim 1, wherein in the formula (1), $R^f$ is a $C_{6-12}$ perfluoroalkyl group.

5. The fluorine-containing organic compound according to claim 1, wherein in the formula (1), $R^f$ is a straight-chain fluoroalkyl group.

6. A fluorine-containing organic compound of the following formula (2):

$$CF_3(CF_2)_n CH_2CH_2CH_2OCH_2CH=CH_2 \quad (2)$$

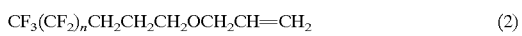

wherein n is an integer of from 0 to 19 representing the number of carbon atoms.

7. The fluorine-containing organic compound according to claim 6, wherein n is an integer of from 5 to 11.

8. A fluorine-containing silicone compound prepared by reacting the fluorine-containing organic compound as defined in claim 1 with a hydrosilicone compound.

9. A fluorine-containing silicone compound prepared by reacting the fluorine-containing organic compound as defined in claim 6 with a hydrosilicone compound.

10. The fluorine-containing silicone compound according to claim 8, wherein the hydrosilicone compound is a compound having an average compositional formula represented by the following formula (3):

$$(R^7)C(H)_d SiO_{(4-c-d)/2} \quad (3)$$

wherein $0 \leq c < 4$, $0 < d < 4$, $0 < c+d \leq 4$, and $R^7$ is a monovalent organic group.

11. The fluorine-containing silicone compound according to claim 9, wherein the hydrosilicone compound is a compound having an average compositional formula represented by the following formula (3):

$$(R^7)_c(H)_d SiO_{(4-c-d)/2} \quad (3)$$

wherein $0 \leq c < 4$, $0 < d < 4$, $0 < c+d \leq 4$, and $R^7$ is a monovalent organic group.

* * * * *